United States Patent [19]

Kopetzki et al.

[11] Patent Number: 6,153,192
[45] Date of Patent: Nov. 28, 2000

[54] PEPTIDES WITH A CHARACTERISTIC ANTIGENIC DETERMINANT OF α1-MICROGLOBULIN

[75] Inventors: Erhard Kopetzki, Penzberg; Christian Klein, Weilheim; Dieter Mangold, Maxdorf; Werner Stock, Gräfelfing; Reiner Schlipfenbacher, Lampertheim, all of Germany

[73] Assignee: Boehringer Mannheim GmbH, Mannheim, Germany

[21] Appl. No.: 08/096,044

[22] Filed: Jul. 22, 1993

Related U.S. Application Data

[62] Division of application No. 07/743,496, Aug. 5, 1991, abandoned.

[30] Foreign Application Priority Data

Aug. 6, 1990 [DE] Germany .............................. 40 24 919

[51] Int. Cl.⁷ .......................... A61K 39/00; A61K 38/00; G01N 33/53; G01N 33/566
[52] U.S. Cl. ....................... 424/184.1; 424/88; 435/7.92; 435/7.93; 435/7.94; 435/7.95; 436/501; 530/326; 530/327; 530/328; 530/329; 530/392; 530/810; 530/812
[58] Field of Search .............................. 424/88; 435/7.92, 435/7.93, 7.94, 7.95; 436/501; 530/326, 327, 328, 329, 392, 810, 812

[56] References Cited

U.S. PATENT DOCUMENTS

| | | | |
|---|---|---|---|
| 4,636,463 | 1/1987 | Altman et al. | 435/7 |
| 5,030,565 | 7/1991 | Niman et al. | 435/70.21 |

FOREIGN PATENT DOCUMENTS

| | | |
|---|---|---|
| 56-106153 | 8/1981 | Japan . |
| 2084317 | 4/1982 | United Kingdom . |

OTHER PUBLICATIONS

Van Regenmontal Immunology Today 10(8): 266–272, 1989.
Monroe (1984) "Immunoassay" Analyt. Chem 56 (8): 921A–931A.
Harlow et al (1988) "Antibodies, A Laboratory Manual" Cold Springs Harbor pp. 128–129.
Babiker–Mohamed et al (Nov., 1991) "Characterical of Monoclonal . . . " Scand. J. Immunol 34:655–666.
Unumeyer et al (1986) "The mRNA for a proteinase . . . " Nucleic Acids Res. 14:7839–7850.
Nilson et al J. Imm. Meth. 99 (1987) 39–45.
Fernandez–Luna J. Imm. Meth. 82 (1985) 101–110.
Vincent et al J. Imm. Meth. 82 (1985) 111–119.
Lerner Nature 299 (1982) 592–596.
Akerstrom et al TIBS 15 (Jun. 1990) 240–243.
Harlow et al *Antibodies A Laboratory Manual* (1988) pp. 342–343 CSH.
Hemmila Clin. Chem. 31 (1985) 359–370.
Traboni et al., Chem. Abst. 105(19): 166095w (1986).
Postmann et al., Chem. Abst. 114(3): 20507w (1991).
Koyamaishi, Patent Abstracts of Japan 5: 177 (1981).

*Primary Examiner*—James C. Housel
*Assistant Examiner*—Rodney P. Swartz, Ph.D
*Attorney, Agent, or Firm*—Fulbright & Jaworski, LLP

[57] ABSTRACT

A peptide according to the present invention is not more than 40 amino acids long and contains a sequence which is at least 6 amino acids long from the amino acid partial sequence between the amino acids 144 and 183 of human α1-microglobulin or/and a sequence which is at least 6 amino acids long from the amino acid partial sequence between the amino acids 1 and 20 of human α1-microglobulin.

An antibody according to the present invention is capable of specific binding to a peptide according to the present invention as well as to human α1-microglobulin.

In order to determine human α1-microglobulin in a sample liquid by an immunoassay, the sample liquid is brought into contact simultaneously or sequentially with defined amounts of the components antibody and peptide whereby one of the components is labelled and the determination is carried out by means of this label.

11 Claims, 3 Drawing Sheets cloning strategy

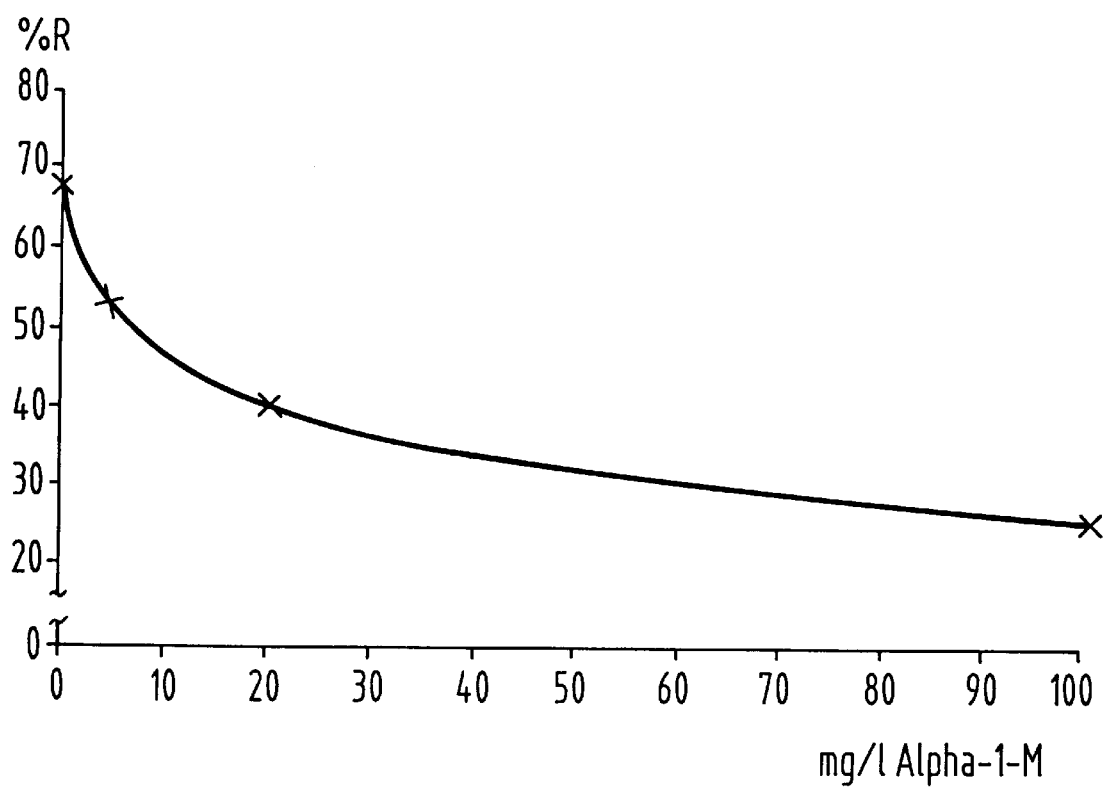

PEPTIDES WITH A CHARACTERISTIC ANTIGENIC DETERMINANT OF α1-MICROGLOBULIN

This application is a divisional, of application Ser. No. 07/743,496, filed Aug. 5, 1991, now abandoned.

The invention concerns peptides and antibodies which can be used in methods for the determination of human α1-microglobulin in a sample liquid by an immunoassay, as well as test carriers for the analytical determination of α1-microglobulin in a sample liquid and finally methods for the analytical examination of a sample liquid using a test carrier according to the present invention.

α1-microglobulin which is also known as protein HC occurs in human serum, in the cerebrospinal fluid and in urine. α1-microglobulin occurs in plasma in a free form as well as in a complex with IgA. It is a member of the α2$\mu$-globin protein family which for example includes the proteins α2$\mu$-globin, β-lactoglobulin, retinol binding protein, apolipoprotein D, the BG protein from the olfactory epithelium and also α1-microglobulin. The biological function of these proteins is presumed to be the binding and transport of small hydrophobic molecules in body fluids (Hunt et al., Biochem. Biophys. Res. Commun. 149 (1987), 282–288; Godovac-Zimmermann, TIBS 13 (1988), 64–66). α1-microglobulin is synthesized as a "prepro" protein with inter-α-trypsin inhibitor and is released by processing (Kaumeyer et al., Nucl. Acids Res. 14 (1986), 7839–7850).

α1-microglobulin (also denoted α1M in the following) is a monomeric protein consisting of 183 amino acids (Kaumeyer et al., Nucl. Acids. Res. 14 (1986), 7839–7850, cf. FIG. 2, aa 20 to aa 202, N-terminus: Gly Pro Val, C-terminus: Ile Pro Arg), which has carbohydrate side chains at the three amino acid positions 5, 17 and 96 and forms a disulphide bridge between $Cys^{72}$ and $Cys^{169}$ (Takagi et al., Biochem. Biophys. Res. Commun. 98 (1981), 997–1001, amino acid positions according to Kaumeyer et al., see above). A chromophore is associated with the α1-microglobulin protein which has not been characterized in more detail and gives the protein a yellow-brown color.

The α1-microglobulin concentration in the urine of healthy individuals is <10 mg/l. When the kidneys are damaged proteins of low molecular weight (Low Molecular Weight Proteins), which include α1-microglobulin with a molecular weight of ca. 30 kD, are only partially reabsorbed and thus pass into the urine to an increasing extent (proteinuria). Concentrations of up to 200 mg/l α1-microglobulin are then attained (Weber et al., Klin. Wochenschr. 63 (1985), 711–717). α1-microglobulin is stable in the clinically relevant pH range of the urine of pH 4 to 10 (Yu et al., J. Clin. Pathol. 36 (1983), 253–259) and can be stored in a stable form at −20° C. (Weber et al., see above). α1-microglobulin thereby becomes a suitable indicator for tubular renal function.

Only methods of determining α1-microglobulin by measurement of turbidity have been known up to now. In such methods the α1M in the sample is for example directly agglutinated with an antibody against α1M which is bound to latex, if desired, and the turbidity which forms is determined nephelometrically. This method can, however, only be carried out with the aid of a nephelometer.

A further method is to visually determine the turbidity which forms in this way against a dark background. This method is, however, time-consuming, requires several steps and only gives a qualitative result.

The use of isolated human α1-microglobulin is disadvantageous for an application in immunoassays since this protein is not a homogeneous substance, it has a considerable charge heterogeneity and, as already described, contains a chromophore which has not been characterized in detail up to now (see Grubb et al., J. Biol. Chem. 258 (1983), 14698–14707). The protein has to be isolated from human material, e.g. urine. As a result it is difficult to produce in large amounts and in constant quality.

The object of the present invention was therefore to eliminate the disadvantages of the state of the art and to provide an α1M test which can be carried out visually and yields a semi-quantitative result or which can be carried out routinely on automated analyzers. For this purpose it is, however, still necessary to provide substances which exhibit immunological properties which are similar to those of α1-microglobulin and therefore can easily be used in an immunological assay for the determination of α1-microglobulin.

This object is achieved according to the present invention by peptides which are not more than 40 amino acids long and contain a sequence which is at least 6 amino acids long from the amino acid partial sequence between the amino acids 144 and 183 of human α1-microglobulin, (SEQ ID NO: 11) whereby they preferably contain a sequence which is at least 6 amino acids long from the partial sequence between the amino acids 158 and 183.

The invention also provides peptides which are not more than 40 amino acids long and contain a sequence which is at least 6 amino acids long from the amino acid partial sequence between the amino acids 1 and 20 of human α1-microglobulin (SEQ ID NO: 12).

Apart from at least 6 amino acids from the special partial sequences of human α1-microglobulin, the peptides according to the present invention can contain further amino acids up to a maximum number of 40 which can be chosen arbitrarily. However, in a preferred embodiment of the invention the additional amino acids are the same as those which adjoin the said at least 6 amino acids in native human α1-microglobulin.

In a preferred embodiment of the present invention the peptide according to the present invention has a carrier protein moiety in addition to the aforementioned amino acids; the peptide according to the present invention is then a fusion protein. Such a fusion protein can be desirable with regard to an increased expression as well as with regard to additional properties which the carrier protein moiety contributes. Thus for example the carrier protein moiety can ensure a favorable localization of the expression product in a host cell so that the isolation is simplified. The production can be carried out according to known methods such as e.g. insertion of a corresponding fused DNA into an expression vector and subsequent expression and isolation of the fusion protein. Within the scope of the invention the carrier protein moiety is preferably the protein sequence of the galactose binding protein GBP which has been shortened by three amino acids. In a further preferred embodiment the carrier protein moiety can contain partial sequences of α1M, preferably up to 20 amino acids. The mglB gene from E. coli which is used for the expression of the carrier protein moiety is cloned and the DNA sequence is known (Müller et al., Mol. Gen. Genet. 185 (1982), 473–480; Scholle et al., Mol. Gen. Genet. 208 (1987), 247–253). Plasmid-coded GBP protein (pVB1 plasmid, Scholle et al., see above) is overexpressed up to an amount of 30% of E. coli total protein after derepression of the mglB promoter. A comparable overexpression was found for GBP fusion proteins which were constructed via the single EcoRI restriction cleavage site located at the 3' end, 12 base pairs before the stop codon of the mglB structural gene. As a result a C-terminal GBP fusion partner which is three amino acids shorter (307 amino acids) is formed. Secreted GBP fusion proteins are soluble and easy to release from the periplasma by osmotic shock without lysis of the host cell (Neu and Heppel, J. Biol. Chem. 254 (1965), 7529–7533). A particularly preferred fusion protein contains the peptide sequences according to the invention which are located within the N-terminal (aa 1–20) sequence as well as within the C-terminal sequence (aa 144–183) in addition to the carrier protein moiety.

The peptides according to the present invention can be synthesized chemically or by incorporating a corresponding DNA sequence into a plasmid and expressing it in a suitable host cell. The peptides according to the present invention are suitable for all areas of application in which although the immunological reactivity of α1-microglobulin is necessary it would nevertheless be advantageous to have a standardized antigen with regard to homogeneity.

In a further preferred embodiment of the invention the peptide is coupled to a partner of a binding pair whereby this is preferably the biotin-(strept)avidin system. Further suitable binding pairs are e.g. haptens and antihapten antibodies which are directed against them.

The invention also provides antibodies which are capable of specific binding to one of the peptides according to the present invention as well as to human α1-microglobulin. Within the scope of the invention these include polyclonal antibodies as well as monoclonal antibodies. In a preferred embodiment of the invention they are, however, monoclonal antibodies. Monoclonal antibodies are in turn particularly preferred which are obtainable from the cell line ECACC 90071906.

In addition the invention also provides a process for the production of the antibodies according to the present invention in which suitable animals are immunized by well-known methods using either native α1-microglobulin or a peptide according to the present invention, antibodies are isolated and those antibodies are selected which are capable of specific binding to native human α1-microglobulin as well as to a peptide according to the present invention.

The process according to the present invention encompasses a process for the production of polyclonal antibodies as well as a process for the production of monoclonal antibodies. Such processes are known to one skilled in the art.

In order to obtain the monoclonal antibodies according to the present invention, laboratory animals such as mice are immunized with human α1-microglobulin which is isolated from the urine of patients. For the immunization the immunogen is administered for example in combination with an adjuvant in the usual way. Aluminium hydroxide together with Bordetella pertussis or Freund's adjuvant are preferably used as the adjuvant. The immunization is preferably carried out over several months with at least four immunizations at 4–6 week intervals (intraperitoneal injection).

B-lymphocytes are isolated from the spleen of the animals immunized in this way and they are fused with a permanent myeloma cell line. The fusion is carried out according to the well-known method of Köhler and Milstein (Nature 256, (1975) 495–497). The primary cultures of hybrid cells which form in this process are cloned in the usual manner e.g. using a commercial cell sorter or by "limited dilution". In each case those cultures are processed further which react positively with isolated α1-microglobulin from the urine of patients or with one of the peptides mentioned in examples 1–8 or 13–14 using a suitable test procedure, for example an enzyme-linked immunoassay (ELISA method). In this way several hybridoma cell lines are obtained which produce the monoclonal antibodies according to the present invention. These cell lines can be cultured according to known methods and the monoclonal antibodies produced by them can be isolated. An example of a cell line obtained in this way is clone 6.046.75 (ECACC 90071906). The cell line is deposited under the stated number at the depositary institution ECACC (European Collection of Animal Cell Cultures).

The selection of the antibodies according to the present invention can be carried out as described in Example 15.

The invention also provides a method for the determination of human α1-microglobulin in a sample liquid by an immunoassay in which the sample liquid is brought into contact simultaneously or sequentially with defined amounts of the components according to the present invention, i.e. antibody and peptide, whereby one of the components is labelled and the determination is carried out by means of this labelling. In this case all known methods of determination are suitable as immunoassays.

Thus for example a labelled antibody according to the present invention can be pre-incubated with the sample liquid whereby the antibody is present in excess of the expected amount of α1-microglobulin in the sample and then the pre-incubated reaction mixture is incubated with a peptide according to the present invention which is coupled to a solid phase and as a result the excess labelled antibody is separated off. After separating the phases, the antibody label can be determined in the liquid phase by which means the amount of α1-microglobulin present in the sample liquid can in turn be deduced. The components can also be incubated simultaneously, in which case, however, the antibody is added in about the same amount as the expected concentration of α1-microglobulin in the sample. Yet another way of carrying out the test is to incubate a peptide according to the present invention which is coupled to a solid phase with a labelled antibody according to the present invention in a first step and then to add the sample liquid which results in a competitive reaction with the α1-microglobulin in the sample for the antibody and a portion of the antibody according to the present invention which was bound to the peptide coupled to the solid phase becomes detached and binds to the α1-microglobulin from the sample. The detection can be carried out on the solid phase as well as in the liquid phase.

A further variant of the test is to couple the antibody according to the present invention to a solid carrier and to incubate it with labelled peptide according to the present invention and sample liquid. By this means the two antigens also compete for the antibody, the detection is carried out via the labelling of the peptide according to the present invention which is coupled to the solid phase via the antibody. Finally it is also possible to carry out the method according to the FPIA technique (fluorescence polarization immunoassay). In this case a peptide according to the present invention labelled with a fluorescent dye is incubated with antibody and with antigen from the sample liquid whereby the peptide label is changed by binding to the antibody.

In a preferred embodiment of the invention, the non-labelled component is bound to a solid carrier material and the determination of the label is carried out after separation of the liquid and solid phase.

According to the present invention an enzyme label, fluorescent dye label, radioactive label, labelling with gold or selenium dioxide or labelling with colored polymers such as e.g. latex particles can be used as the label. However, it is preferred according to the present invention to use an enzyme as label and to detect this enzyme by means of an enzymatic colour-forming reaction.

Particularly preferred enzymes are in this case β-D-galactosidase, alkaline phosphatase or peroxidase, which are for example detected by means of the substrates chlorophenol red-β-D-galactoside, p-nitrophenol phosphate and ABTS®. In another preferred embodiment of the invention the label used is a fluorescent dye whose fluorescent quantum yield or capability to depolarize is changed by binding to the antibody and depends on the concentration of the α1-microglobulin contained in the sample liquid.

In the method according to the present invention it is preferred to use a monoclonal antibody as antibody. The coupling of the one component to the solid phase is preferably carried out by means of a specific binding pair and namely in such a way that a part of the specific binding pair is anchored to the solid carrier and the other part of the binding pair is coupled to the component. A particularly preferred specific binding pair within the scope of the invention is the biotin-(strept)avidin system.

It is also preferred to carry out the test reaction in microtitre plates or test tubes and the one component is bound to the bottom of the wells or to the walls of the test tubes which serve as the solid carrier material.

The invention also concerns a test strip for the analytical determination of α1-microglobulin in a sample liquid with several zones consisting of capillary-active material which are arranged side by side on a base layer and are in liquid contact with one another which is characterized in that it comprises a first reagent system in a reaction zone which contains one of the components antibody according to the present invention and peptide according to the present invention in an immobilized form and the other component in a labelled form and has a detection area which optionally comprises a second reagent system which enables the determination of the label of the other component. Since the zones of the test strip according to the present invention are in liquid contact with one another they form a liquid transport path along which a liquid, driven by capillary forces, flows from the reaction zone to the detection area. In this process the sample liquid is brought into contact simultaneously or sequentially with defined amounts of the components antibody and peptide according to the present invention whereby one of the components is labelled and the determination is carried out on the detection area by means of this label. In the following the labelled component is also denoted conjugate.

Such test carriers, their components and the basic experimental procedure using test carriers is described in general in EP-A 0 374 684, EP-A 0 353 570 and EP-A 0 353 501 and reference is hereby made to them. The test carriers according to the present invention are, however, designed for the specific determination of α1-microglobulin and therefore contain an appropriate antibody according to the present invention.

The above-mentioned EP-A 0 374 684, EP-A 0 353 570 and EP-A 353 501 should also be referred to with regard to the materials which can be used to construct the test carrier.

In the test strip according to the present invention a combination of an immobilized antibody with a labelled peptide according to the present invention as a conjugate or an immobilized peptide according to the present invention and a labelled antibody as a conjugate is preferably used.

The test strip according to the present invention essentially consists of two parts i.e. the reaction zone and the detection area.

The sample liquid is taken up in the reaction zone. In a preferred embodiment of the invention the reaction zone contains further substances which can aid in adjusting the conditions for an optimal reaction process (e.g. ionic strength, pH value). The immunological reaction between antibody and α1-microglobulin from the sample also takes place in the reaction zone. As a result of this reaction an amount of labelled conjugate which correlates with the amount of α1M in the sample reaches the detection area and is detected there by means of the label using an appropriate detection procedure (e.g. fluorescence or reflectance).

The reaction zone of the test strip according to the present invention consists of one or several capillary-active detection areas which are essentially arranged side by side and are in fluid contact with one another so that they form a liquid transport path along which a liquid, driven by capillary forces, flows through the reaction zone to the detection area. The number of areas of the reaction zone is not critical and depends on whether the necessary reagents for the immunological reaction should be applied to separate or common areas. Thus it is possible to apply all reagents to a single area or to separate the reaction zone into different areas, for example a starting area, a buffer area, a conjugate area and a capture area which then have to be arranged sequentially. Neighbouring areas can also be combined at random. For example the buffer area and conjugate area or the absorptive area, buffer area and conjugate area can together form one area.

In a preferred embodiment the test strip according to the present invention is therefore constructed in such a way that the reaction zone is divided into different areas which are arranged sequentially in the direction of the detection area in the sequence starting area, buffer area, conjugate area and capture area whereby the sample liquid is taken up in the starting area, the buffer area has the substances which optimize the reaction process, the conjugate area contains the labelled component and the capture area contains the immobilized component of the first reagent system, and neighboring areas can be combined at random with one another in the above-mentioned sequence.

In this embodiment the test strip according to the present invention contains, if desired, a starting area as the first area. The starting area makes contact with the sample liquid. It is made in such a way that it can spontaneously and completely take up a liquid and readily releases it or passes it on. In order to ensure this the test strip can remain, for example during the determination, with the starting area continuously immersed in the sample liquid.

The buffer area which is, if desired, separated from the starting area contains auxiliary substances which produce the conditions for an optimal reaction process (e.g. ionic strength, pH value). The buffer area consists of porous material and is preferably made of a fleece based on cellulose, polyester or nylon.

The conjugate area is, if desired, adjacent to the buffer area. The conjugate area essentially contains the conjugate of label and antibody against α1-microglobulin or peptide according to the present invention in a detachable form. Suitable carrier materials and methods for applying the conjugate are for example described in EP-A-0 353 570. Porous materials based on polyester, cellulose or glass fibre are particularly suitable.

The capture area is, if desired, adjacent to the conjugate area. This contains the peptide according to the present invention in a bound form if a conjugate of antibody and label is used as the conjugate, or it contains an immobilized antibody if a conjugate of peptide according to the present invention and label is used as the conjugate. The immobilization can be carried out according to known methods, for example chemically or by immunoprecipitation. However, a biological binding partner such as e.g. (strept)avidin is preferably bound to the material of the capture area and the antibody or the peptide according to the present invention which is bound to the other biological binding partner, for example biotin, is added. The immobilization of the peptide or the antibody according to the present invention is then achieved via binding of the biological binding partner (e.g. biotin/streptavidin binding). Such immobilization methods are described for example in EP-A 0 374 684.

In a preferred embodiment at least the conjugate area and buffer area are combined. In a further preferred embodiment at least the conjugate area and the capture area are combined. In this case the conjugate, i.e. the labelled component, is already bound to the immobilized component in a prior immunological reaction. After addition of the sample, the α1-microglobulin contained in the sample displaces a partial amount of the conjugate or, when the labelled antibody is used as the conjugate, it displaces this from the immobilized peptide in a displacement reaction. This displaced conjugate then migrates into the detection area and is detected there.

In a further preferred embodiment the reaction zone contains at least two separate areas. The optimal conditions for the reaction process are set up in the first area (buffer/conjugate area) and here the immunological reaction between the α1-microglobulin from the sample and the labelled antibody takes place. In the second area of the reaction zone (capture area) the reaction with the immobilized partner of the immunological reaction takes place whereby an amount of conjugate remains in solution which correlates with the amount of α1-microglobulin contained in the sample and is transported to the detection area.

The detection area, and if desired its capture area, is adjacent to the reaction zone. If desired, this can preferably be placed partially on or above the capture area (cf. EP-A 0 353 500). The detection area preferably contains a reagent system with a suitable test substrate for the label which undergoes a change on contact with the labelled component which can be observed or when using a label which can be directly determined (e.g. fluorescent labelling) it serves to directly detect the conjugate. If a substrate is included then this zone preferably consists of a dissoluble film or a fabric or fleece which is sealed hydrophobically. Such carriers are described for example in EP-A 0 353 501. By this means the sample liquid elutes the substrate from the carrier when it reaches the end of the zone and starts the test reaction.

Such test strips are also described in EP-A 0 374 684 to which reference is herewith made.

The invention also concerns the use of a test strip according to the present invention for the determination of α1-microglobulin in a sample liquid in which the sample liquid is applied to the reaction zone or the starting zone if present and the determination is carried out via the labelling of the labelled component which reaches the substrate area.

By means of the peptides and antibodies according to the present invention and their application in methods for the qualitative and quantitative determination of α1-microglobulin in a sample liquid as well as the test strips provided according to the present invention for carrying out this test, a test system for kidney function can be provided in a simple manner which is characterized by the amount of α1-microglobulin in the urine. Such a test strip according to the present invention as well as the determination using such a test strip in a form suitable for screening examinations enables information to be obtained rapidly on a possible impairment of kidney function. For this purpose urine as the sample liquid is for example merely brought into contact with the reaction zone of the test strip and after a certain exposure time the change in color is determined in the detection area.

The following examples elucidate the invention further in conjunction with the sequence protocols and figures.

SEQ ID NO. 1 Oligodeoxynucleotides (Example 2.1) used for the gene synthesis of the C-terminal region of α1M (aa 161–183)

SEQ ID NO. 2 DNA sequence of the mglB-Δα1M C-fusion gene and the protein sequence derived therefrom of the GBP-Δα1M C-fusion protein (Example 2.1)

SEQ ID NO. 3–8 Oligodeoxynucleotides (Example 2.2) used for the gene synthesis of partial regions of the α1-microglobulin gene (aa 54–87)–(aa 161–183)

SEQ ID NO. 9 DNA sequence of the mglB-Δα1M fusion gene and of the protein sequence derived therefrom of the GBP-Δα1M fusion protein (Example 2.2)

BRIEF DESCRIPTION OF DRAWINGS

FIG. 3 Calibration curve for an α1M test strip

Standard methods were used for the manipulation of DNA such as those described by Maniatis et al., in Molecular Cloning, Cold Spring Harbor Laboratory Press, Cold Spring Harbor, N.Y. (1989).

Abbreviations:

ABTS®: 2,2'-azino-di-[3-ethylbenzthiazoline sulfonic acid (6)]diammonium salt

SDS: sodium dodecylsulphate aa: amino acid

Tween® 20: polyethoxysorbitan laurate

POD: peroxidase

BSA: bovine serum albumin

Fc : Fc fragment of IgG

Mtr: methoxytrimethylphenylsulphonyl

Ot Bu: oxytertiary butyl

St Bu: tert. butylsulfenyl

EXAMPLE 1

Construction of the Basic Expression Plasmid pVB1/EH (DSM 6081)

The pVB1 plasmid or plasmids derived therefrom is used for the expression of hybrid proteins. pVB1 contains the 2.3 kbp long EcoRI/PvuII vector fragment from the E. coli plasmid pBR322 (ampicillin resistance, origin of replication) and additionally a 2.2 kbp long EcoRI/SmaI fragment which codes for the complete mglB gene from E. coli (Scholle et al., Mol. Gen. Genet 208 (1987) 247–257). The single EcoRI restriction cleavage site located at the 3' end, 12 bp in front of the stop codon, is used to construct fusion proteins.

Figure 1:
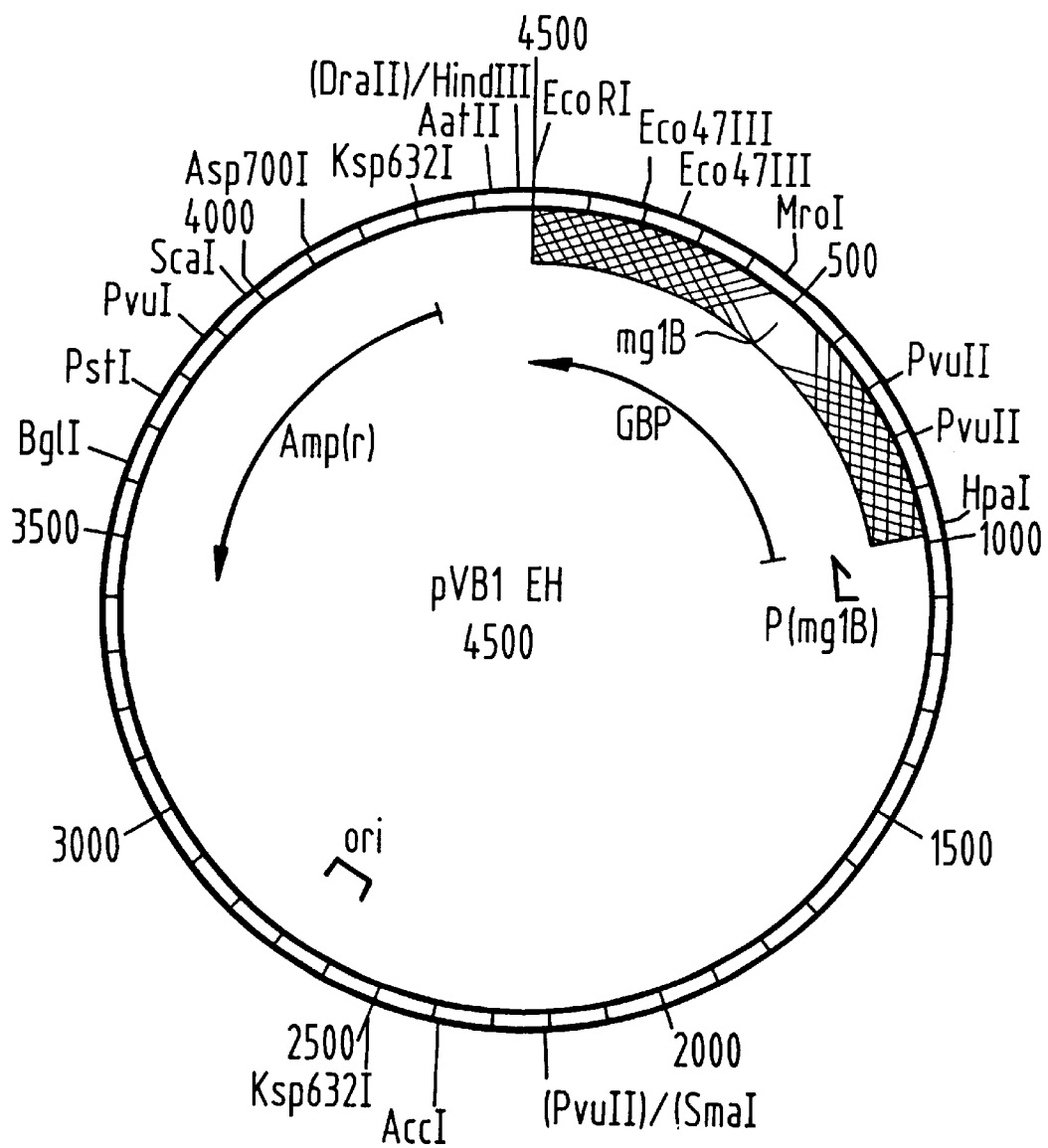
FIG. 1 Plasmid pVB1 EH

In order to construct GBP fusion proteins (insertion of EcoRI/HindIII fragments) the single DraII restriction cleavage site in the pVB1 plasmid was filled up with Klenow polymerase and ligated with the HindIII linker (d(CGAAGCTTCG)) (construction: pVB1/EH; FIG. 1).

EXAMPLE 2

Construction, Expression and Secretion of GBP-Δα1-microglobulin (GBP-Δα1M) fusion proteins

2.1 GBP (aa 1–306)-α1M(aa 161–183) Fusion Protein

The C-terminal region of the α1-microglobulin gene (amino acid position: 161–183) was produced by means of hybridization (reaction buffer: 12.5 mmol/l Tris/HCl, pH 7.0 and 12.5 mmol/l $MgCl_2$) from two chemically synthesized oligodeoxy-nucleotides (SEQ ID NO. 1).

Afterwards the "DNA adapter" was ligated into the ca. 4.5 kbp long pVB1/EH EcoRI/HindIII vector fragment (construction: pVB1/EH-Δα1M-C). The DNA sequence of the adapter was confirmed by means of DNA sequencing. The GBP-Δα1M-C fusion protein and the coding DNA sequence are shown in detail in SEQ ID NO. 2.

2.2 GBP (aa 1–306)-α1M(aa 54–87)-α1M(aa 161–183) Fusion Protein

2.2.1 Chemical Synthesis of Partial Regions of the α1-Microglobulin Gene

Figure 2:
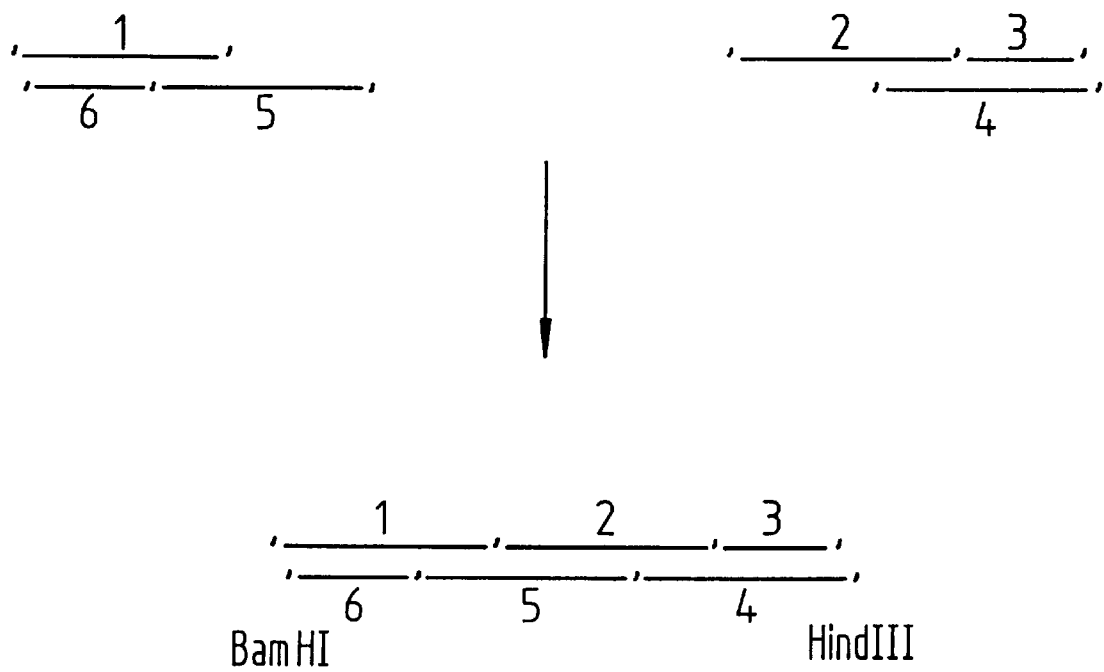
FIG. 2 Strategy for the gene synthesis of α1-microglobulin partial regions (Example 2.2)

A middle (aa 54–87) and selected C-terminal (aa 161–183) region of the α1-microglobulin gene (ca. 200 bp) was synthesized from 6 oligodeoxy-nucleotides in direct fusion. In each of two reaction mixtures three complementary oligodeoxynucleotides were annealed and the two desired hybridization products were purified by gel electrophoresis. After again annealing the two isolated ca. 100 bp long gene blocks, a ca. 200 bp long gene block with a single BamHI and HindIII restriction cleavage site at the 5' end or 3' end was ligated into the ca. 4 kbp long pBR322 HindIII/BamHI vector fragment (construction: pBR322-Δα1M). Afterwards the insert was sequenced. The oligodeoxynucleotides used and the cloning strategy are shown in SEQ ID NO. 3–8 and FIG. 2. The gene synthesis was carried out in accordance with the method published by Wosnik et al. (Gene 60 (1987) 115–127).

2.2.2 Construction of the Plasmid pVB1/EH-Δα1M

The plasmid pBR322-Δα1M was digested with BamHI, the protruding 5' ends of the BamHI cleavage site were filled up with Klenow polymerase and the DNA ends were provided with a suitable EcoRI linker (d (CCGGAATTCCGG)). Afterwards it was cleaved again with EcoRI and HindIII and the ca. 200 bp long EcoRI/HindIII fragment was ligated into the ca. 4.5 kbp long pVB1/EH EcoRI/HindIII vector fragment (construction: pVB1/EH-Δα1M). The GBP-Δα1-microglobulin fusion protein and the coding DNA sequence are shown in SEQ ID NO. 9.

2.3 Expression of the Fusion Proteins in E. coli

The E. coli K12 strain RM82lac$^+$ (met$^+$, lac$^+$ revertant of ED8654; Murray et al., Mol. Gen. Genet. 150 (1977) 53–61, DSM 5446) was used as the host strain. This strain was transformed with the plasmid pVB1/EH-Δα1M or pVB1/EH-Δα1M-C and grown under repressive conditions in DYT medium (1.6% bactotryptone (Difco), 1% yeast extract (Difco), 0.5% NaCl) at 30° C. with 50 mg/l ampicillin and 1% glucose up to an optical density of 5 to 8 at 550 nm. In order to derepress the mglB promoter the centrifuged cells from 1 vol. fermentation medium were transferred into 5 to 10 vol. fresh DYT medium containing 50 mg/l ampicillin but no glucose and derepressed for 14 to 20 hours. Afterwards the cells were harvested from 1 ml of this derepression medium and the expression and cell localization of the GBP-Δα1M fusion protein was characterized by cell fractionation and SDS PAGE and Western blot analysis as described in Example 3. For the cell fractionation the periplasmatic proteins are released by osmotic shock from the E. coli cells (Neu and Heppel, J. Biol. Chem. 254 (1965) 7529–7533) and the remaining cell pellet is lysed as described in Example 3 (cell fractions: a) periplasmatic proteins; b) remaining soluble E. coli proteins; c) insoluble E. coli proteins which can be extracted with chaotropic reagents).

The fusion proteins were synthesized like the natural plasmid-coded GBP protein (308 aa) in the investigated host strain in an amount up to 30% of the E. coli total protein. They are secreted up to >90% into the periplasma, they were soluble, did not aggregate and could be released by osmotic shock from the cells. The α1-microglobulin epitopes of the GBP-Δα1M fusion proteins were recognized by polyclonal (α1M antisera from the Dacopatts Company and the Serotec Company) and monoclonal antibodies which were directed towards natural α1M protein.

2.4 Isolation of the GBP-Δα1M Fusion Protein

RM82lac$^+$ cells which had been transformed with the plasmid pVB1/EH-Δα1M were grown in a 5 l fermenter on the basis of experience with cultures in 5 ml roller cultures or shaking cultures (see above) (yield of biomass: ca. 20 g/l wet weight), the GBP-Δα1M fusion protein was released from the cells by osmotic shock (Neu and Heppel, J. Biol. Chem. 254 (1965) 7529–7533) and the remaining cells were removed by centrifugation. After this simple but very efficient purification step the desired GBP-Δα1M fusion protein can easily be purified to homogeneity by well-known protein purification steps such as e.g. ion exchange chromatography, chromatofocussing, HIC chromatography (hydrophobic interaction chromatography), gel filtration, affinity chromatography and precipitations. The GBP-Δα1M fusion protein was purified to >95% purity from the filtered (nitrocellulose filter, pore diameter 0.45 μm) "osmotic shock preparation" by chromatofocussing (equilibration buffer: 25 mmol/l piperazine-HCl, pH 5.5; pH range: 5→4) followed by hydrophobic chromatography on phenylsepharose (equilibration buffer: 10 mmol/l Tris-HCl, pH 7.0 with 40% ammonium sulphate (AS saturation value relates to 4° C.); elution gradient: 40%→0% AS, 0%→70% ethylene glycol (v/v) in 10 mmol/l Tris-HCl elution buffer, pH 7.0) and a dialysis.

EXAMPLE 3

Cell Lysis, SDS Polyacrylamide Gel Electrophoresis (PAGE) and Western Blot Analysis The cell pellet from 1 ml centrifuged culture medium was resuspended in 0.25 ml 10 mmol/l phosphate buffer, pH 6.8 and 1 mmol/l EDTA and the cells were lysed by ultrasonication. After centrifugation, ⅕ volume 5×SDS-sample buffer (1×SDS-sample buffer: 50 mmol/l Tris-HCl, pH 6.8, 1% SDS, 1% mercaptoethanol, 10% glycerol, 0.001% bromophenol blue) was added to the supernatant, the insoluble cell debris fraction was resuspended in 0.3 ml 1×SDS-sample buffer containing 6 to 8 mol/l urea, the samples were incubated for 5 minutes at 95° C. and centrifuged. Afterwards the proteins were fractionated by SDS polyacrylamide gel electrophoresis (Laemmli, Nature 227 (1970) 680–685) and stained with Coomassie Brilliant Blue R.

As an alternative and in parallel, the electrophoretically fractionated proteins were transferred to nitrocellulose filters, immobilized (Towbin et al., Proc. Natl. Acad. Sci. 76 (1979) 4350) and the immune-reactivity of GBP-Δα1M fusion proteins was determined with polyclonal and/or monoclonal anti-α1M antibodies.

EXAMPLE 4
Determination of Immune Reactivity of Chemically Synthesized Partial Regions of the α1M Protein by Polyclonal Anti-α1M Antibodies Microtitre plates (Nunc) were incubated with 100 µl/well of a solution of 5 µg/ml polyhapten (produced according to Examples 10, 12 and 14) in phosphate buffer, pH 9.6 for 20 hours at room temperature. After washing (washing solution 0.9% NaCl, 0.1% Tween® 20), antiserum against α1M (from sheep, immunized with α1M isolated from urine) in sample buffer (0.1 mol/l phosphate buffer pH 7.4, 0.9% NaCl, 0.1% Tween® 20) was added in increasing dilutions. The antisera were diluted in phosphate buffer pH 7.4 containing 0.9% NaCl and 0.1% Tween® 20.

125 µl diluted antiserum was added, incubated for one hour at room temperature while shaking and subsequently washed three times with washing buffer. 100 µl conjugate of POD and polyclonal antibody against sheep Fcγ (10 U/l) was added.

The substrate solution was added (100 mmol/l phosphate-citrate buffer pH 4.4, 3.2 mmol/l sodium perborate, 9 mmol/l ABTS®).

It was incubated for 30 minutes at room temperature and the color formation was measured with an ELISA reader at 405 nm.

For the evaluation the absorbance (y axis linear) was plotted semi-logarithmically against the corresponding antiserum dilution (x axis logarithmic). The titre of the antiserum was determined from the half maximum absorbance.

An average titre of 1:3200 was obtained when using the polyhapten from a C-terminal peptide (Example 10). When a polyhapten from a N-terminal peptide (Example 14) was used an average titre of 1:3200 was also obtained. When a peptide from the middle region of α1M (Example 12) was used, a titre was obtained which was no longer significant.

EXAMPLE 5
Determination of α1-microglobulin in Microtitre Plates

Microtitre plates (Nunc) were incubated with a solution of thermo BSA-streptavidin (produced according to EP-A 0 269 092, 100 ng/ml; 300 µl/well) for 20 hours at room temperature. After washing (3× with washing solution: 0.9% NaCl, 0.1% Tween® 20), 350 µl/well of a solution of 0.9% sodium chloride, 0.3% bovine serum albumin and 2% sucrose was added and incubated for 30 minutes at room temperature. Subsequently it was washed three times with washing solution.

100 µl biotinylated fusion protein, biotinylated according to Anal. Biochem. 154 (1986) 368, (25 ng/ml) was added per well and shaken for one hour at room temperature. Subsequently it was washed three times with washing solution.

100 µl of a solution of a monoclonal antibody against α1-microglobulin (concentration ca. 5 to 10 ng/ml) was added, shaken for one hour at room temperature and washed three times with washing solution.

100 µl of sample which contains α1-microglobulin, was added per well, shaken for 10 minutes at 37° C. and washed three times with washing solution.

100 µl of a solution of a conjugate, consisting of peroxidase and a polyclonal sheep antibody against mouse Fc γ, was added per well (peroxidase activity 25 mU/ml) and shaken for one hour at room temperature. Subsequently it was washed three times with washing solution and 100 µl substrate solution (1 mg/ml ABTS® in 100 mmol/l phosphate-citrate buffer, pH 4.4, 3.2 mmol/l sodium perborate, 2.5 mmol/l $H_2O_2$) was added per well and shaken for 50 minutes at room temperature. Afterwards the absorbance was measured at 405 nm. The biotinylated peptide from Example 8 can be used in a similar way instead of the biotinylated fusion protein.

EXAMPLE 6
Synthesis of Peptide 1 (SEQ ID NO: 13) HCys(StBu) ValProGlyGluGlnGluProGluProIleLeuIleProArgOH The peptide was synthesized by solid phase synthesis using the fluorenylmethoxycarbonyl (Fmoc) group as a permanant alpha amino protecting group as described by Meienhofer et al., Int. J. Peptide Protein Res. 13, 35–42 (1979). The semiautomatic peptide synthesizer SP 640 from the Labortec Company, Bubendorf (Switzerland) was used as an aid to synthesis.

The Fmoc amino acids were obtained from the Bachem Company, Bubendorf (Switzerland).

The C-terminal Fmoc amino acid, FmocArg(Mtr)OH, was coupled to p-alkoxybenzylalcohol resin (Bachem Company, Bubendorf, Switzerland) as described by Meienhofer.

| Protocol for a synthetic cycle | | |
|---|---|---|
| Step | Time | Reagent/solvent |
| 1 | 2 * 1 min | DMF (dimethylformamide) |
| 2 | 1 * 3 min | piperidine/DMF 1:4 |
| 3 | 1 * 7 min | piperidine/DMF 1:4 |
| 4 | 4 * ½ min | DMF |
| 5 | 2 * ½ min | isopropanol |
| 6 | stop | ninhydrin test |
| 7 | 2 * 1 min | DMF |
| 8 | stop | addition of the next Fmoc-amino acid and HOBt (1-hydroxy-benzotriazol) in DMF |
| 9 | 2 min | shaking |
| 10 | stop | addition of DCC (dicyclohexyl-carbodiimide) |
| 11 | 90 min | coupling |
| 12 | 3 * 1 min | DMF |
| 13 | 2 * 1 min | isopropanol |
| 14 | stop | ninhydrin test |

The Fmoc-amino acids and DCC are each used for the coupling according to steps 8–11 in a three-fold molar amount relative to the loading of the starting resin; HOBt is used in a 4.5-fold molar amount.

1 g starting resin, FmocArg(Mtr)p-alkoxybenzyl alcohol resin, with a loading level of 0.4 mmol/g are used for the synthesis of peptide 1. In the synthetic cycles the following Fmoc-amino acids are used:

1.) FmocProOH; 2.) FmocIleOH; 3.) FmocLeuOH;

4.) FmocIleOH; 5.) FmocProOH; 6.) FmocGlu(OtBu)OH;

7.) FmocProOH; 8.) FmocGlu(OtBu)OH; 9.) FmocGlnOH;

10.) FmocGlu(OtBu)OH; 11.) FmocGlyOH; 12.) FmocProOH;

13.) FmocValOH; 14.) FmocCys(StBu)OH.

After coupling the last Fmoc-amino acid, steps 1–5 of the synthetic cycle are carried out to cleave off the Fmoc protecting group. Afterwards the peptide is separated from the resin as described by Sieber, Tetrahedron Letters 28, 1637 (1987).

The crude product is purified preliminarily on Sephadex® G-10 (eluant 0.1% acetic acid) and then chromatographed on Polygosil® C18, 5 µm (Macherey & Nagel) (gradient: 0.1% trifluoroacetic acid in water up to 65% isopropanol in water, 0.1% trifluoroacetic acid).

Yield: 177 mg peptide 1; $MH^+$ in FAB mass spectrum: 1765

EXAMPLE 7
Synthesis of Peptide 2 (SEQ ID NO: 14) HCysValProGly-GluGlnGluProGluProIleLeuIleProArgOH In order to cleave off the cysteine protecting group, peptide 1 obtained according to Example 6 is dissolved in 130 ml 0.1 molar potassium phosphate buffer pH 8.5, degassed several times and aerated each time with nitrogen. 780 mg dithiothreitol is then added to the solution and it is left to stand for 24 hours under nitrogen.

Subsequently it is acidified to pH 5 with hydrochloric acid and chromatographed by chromatography on Polygosil® C18 as described in Example 6.

Yield: 133 mg peptide 2

EXAMPLE 8
Synthesis of Peptide 3 (SEQ ID NO: 5) biotinyl-6-aminocaproyl-Cys(StBu) ValProGlyGluGlnGluProGluProIleLeuIleProArgOH 250 mg peptide 1 is dissolved in 50 ml 0.1 molar potassium phosphate buffer pH 8.5. A solution of 392.7 mg biotinyl-6-aminocaproic acid N-hydroxy-succinimide ester in 12 ml DMF is added and stirred for 40 hours. It is lyophilized and chromatographed as described in Example 6 on Polygosil® C18.

Yield: 110 mg peptide 3

EXAMPLE 9
Synthesis of Immunogen 1 from Peptide 2 and Edestin 5 g edestin from hemp seed (Roth) is stirred into 500 ml 0.1 molar potassium phosphate buffer, pH 7.0 and a solution of 500 mg maleimidohexanoic acid-N-hydroxysuccinimide ester in 100 ml ethanol is added. The solution is stirred for 90 minutes at room temperature, the solid is aspirated, washed twice with 100 ml water each time, four times with 100 ml ethanol each time and again twice with 100 ml water each time. The solid is suspended in 150 ml water and lyophilized.

Yield: 4.34 g maleimidohexanoyl-edestin 155 mg maleimidohexanoyl-edestin and 42 mg peptide 2 are suspended under argon in 15 ml 0.05 molar potassium phosphate buffer, pH 6.5 and stirred for 2.5 days at room temperature. It is centrifuged, the residue is washed with 50 ml water and the residue suspended in 20 ml is then dialysed against water.

80 mg immunogen 1 is obtained after lyophilization.

EXAMPLE 10
Synthesis of Polyhapten 1 from Peptide 2 and Bovine Serum Albumin 1 g bovine serum albumin is dissolved in 30 ml 0.1 molar potassium phosphate buffer, pH 7.5. 226 mg succinimidyl-pyridyldithiopropionate dissolved in 15 ml ethanol is added to the solution. It is stirred for 40 minutes at room temperature and the entire reaction solution is chromatographed on Ultrogel ACA 202 (31*3 cm); (JBF, Villeneuve, France) eluant: 0.1 molar potassium phosphate buffer, pH 6.0.

152 ml of a solution of pyridyldithiopropionyl-bovine serum albumin is obtained at a concentration of c=6.6 mg/ml=0.096 µmol/ml in 0.1 molar potassium phosphate buffer, pH 6.0.

10 mg peptide 2 and 1.75 ml of the pyridyldithio-propionyl-bovine serum albumin solution are stirred under argon for 12 hours. It is diluted with 6 ml 0.1 molar potassium phosphate buffer, pH 6.0 and chromatographed as described above on a column of Ultrogel® ACA 202.

One obtaines 10 ml of a solution of polyhapten 1 at a concentration of 0.93 mg/ml in 0,1 molar potassium phosphate pH 6.0.

EXAMPLE 11
Synthesis of Peptide 4 (SEQ ID NO: 16) HCysGlyAlaTyr-GluLysThrAspThrAspGlyLysPheLeuTyrHisLysSer LysOH HCys(SEQ ID NO: 17)(StBu) GlyAlaTyrGluLysThrAspThrAspGlyLysPheLeuTyrHis LysSerLysOH is produced by solid phase synthesis analogous to Example 6.

1 g FmocLys(Boc)p-alkoxybenzyl alcohol resin at a loading level of 0.44 mmol/g is used as the starting resin. The following Fmoc-amino acids are used in the synthetic cycles:

1.) FmocSer(tBu)OH; 2.) FmocLys(BOC)OH;
3.) FmocHis(Trt)OH; 4.) FmocTyr(tBu)OH; 5.) FmocLeuOH;
6.) FmocPheOH; 7.) FmocLys(BOC)OH; 8.) FmocGlyOH;
9.) FmocAsp(OtBu)OH; 10.) FmocThr(tBu)OH;
11.) FmocAsp(OtBu)OH; 12.) FmocThr(tBu)OH;
13.) FmocLys(BOC)OH; 14.) FmocGlu(OtBu)OH;
15.) FmocTyr(tBu)OH; 16.) FmocAlaOH; 17.) FmocGlyOH;
18.) FmocCys(StBu)OH:

Afterwards the procedure for cleaving off the peptide from the resin and for the purification is the same as in Example 6. After the Sephadex G-10 column, 454 mg crude peptide is obtained. 50 mg of this is purified on Polygosil C18.

Yield: 5.3 mg peptide HCys(StBu) GlyAlaTyrGluLysThrAspThrAspGlyLysPheLeuTyrHisLysSerLysOH 205 mg HCys(StBu) GlyAlaTyrGluLysThrAspThrAspGlyLysPheLeuTyrHisLysSerLysOH is treated analogous to Example 7 with 277 mg dithiothreitol and processed further.

Yield: 171.6 mg peptide 4

EXAMPLE 12
Synthesis of Polyhapten 2 from Peptide 4 and Bovine Serum Albumin 5 g bovine serum albumin is dissolved in 30 ml 0.1 molar potassium phosphate buffer, pH 6.0. A solution of 447 mg maleimidohexanoic acid-N-hydroxysuccinimide ester in 2 ml DMF is added to this. It is stirred for 1.5 hours and the entire reaction solution is chromatographed on Ultrogel ACA 202 (45*5 cm); eluant 0.1 molar potassium phosphate buffer, pH 6.0. One obtains 184 ml of a solution of maleimidohexanoyl-bovine serum albumin, c=27.5 mg/ml.

110 mg of this solution is reacted under argon for 15 hours with 69.9 mg peptide 4 in 10 ml 0.1 molar potassium phosphate buffer, pH 6.0. The solution is chromatographed on ACA 202 as in Example 10.

EXAMPLE 13
Synthesis of peptide 5 (SEQ ID NO: 18) HGlyProValPro-ThrProProAspAsnIleGlnValGlnGluAsnPheCysOH Peptide 5 is produced analogous to Example 6 by solid phase synthesis.

5 g FmocCys(Trt)p-alkoxybenzyl alcohol resin, at a loading level of 0.68 mmol/g, is used as the starting resin. The following Fmoc-amino acids are used in the synthetic cycles:

1.) FmocPheOH; 2.) FmocAsnOH; 3.) Fmocglu(OtBu) OH;
4.)FmocGlnOH; 5.) FmocValOH; 6.) FmocGlnOH;
7.) FmocIleOH; 8.) FmocAsnOH; 9.) FmocAsp(OtBu) OH;

10.) FmocProOH; 11.) FmocProOH; 12.) FmocThr(tBu)OH;

13.) FmocProOH; 14.) FmocvalOH; 15.)FmocProOH;

16.) FmocGlyOH

Cleavage from the resin and purification of the peptide is analogous to Example 6. Peptide 5 is obtained; MH⁻ in FAB mass spectrum: 1854

EXAMPLE 14

Synthesis of Polyhapten 3 from Peptide 5 and Bovine Serum Albumin 70 ml polyhapten 3, c=0.5 mg/ml is obtained analogous to Example 12 from 4.5 ml of the maleimidohexanoyl-bovine serum albumin solution and 33 mg peptide 5.

EXAMPLE 15

Isolation of Monoclonal Antibodies Against Human α1-microglobulin

Balb/c mice, 8–12 weeks old, are immunized intraperitoneally with 100 μg α1-M (isolated from the urine of patients) or peptide immunogen (produced according to Example 9) or fusion protein as immunogen (produced according to Example 2) together with complete Freund's adjuvant. After 6 weeks, three further immunizations are carried out at intervals of 4 weeks. In each case 100 μg immunogen adsorbed to aluminium hydroxide and *Bordetella pertussis* are administered intraperitoneally. Blood is collected one week after the last immunization and the antibody titre is determined in the serum of the laboratory animals. If the immunization proceeds positively, a fusion is carried out. Four days before the fusion the mice are once again each immunized intravenously with 100 μg immunogen in phosphate-buffered saline. As described by Galfre, (Methods in Enzymology, 73 (1981) page 3) 1×10$^8$ spleen cells of an immunized mouse are mixed with 2×10$^7$ myeloma cells (P3×63Ag8-653, ATCC-CRL 8375) and fused with PEG solution. The fused cells are plated out with 5×10$^4$ cells per well in 24-well plates (Nunc Co.) and cultured in selection medium (hypoxanthine/azaserine medium). After 7–10 days, when clone growth is visible, the culture supernatant of the primary culture is tested for specificity (recognition of α1M, peptides or fusion proteins) using an ELISA procedure. The primary cultures which contain the antigen-specific antibody go into the single cell receptacle with the aid of a fluorescence-activated cell sorter. The hybridoma cell line, clone 6.046.75, could be isolated in this way (ECACC No. 90071906; immunogen: α1M from urine of patients).

The determination of the specificity of the antibodies is carried out as follows:

In order to detect the presence and specificity of antibodies against α1-microglobulin/peptide/fusion protein in the serum of immunized mice or in the culture supernatant of the hybrid cells an ELISA method is used as the basis for the test.

Test 1:

Investigation of antibody binding to isolated native α1-microglobulin.

Microtitre plates (Nunc Co.) are coated with 400 ng/ml polyclonal anti-α1-microglobulin immunoglobulin (sheep anti-human α1-microglobulin, Serotec Co.) in coating buffer (0.2 mol/l sodium carbonate/sodium bicarbonate, pH 9.4). They are re-coated with 0.9% sodium chloride solution and 1% bovine serum albumin. After washing with washing solution (0.9% sodium chloride solution) they are incubated with 50 μg/ml antigen (isolated human α1-microglobulin from urine). After another washing step, the antibody sample (mouse serum or culture supernatant) is added and they are again washed after the incubation. A polyclonal sheep-anti-mouse Fcγ, Fab-peroxidase conjugate (Boehringer Mannheim GmbH, 25 mU/ml) is used as the detection antibody. After a further washing step with washing solution the peroxidase activity is determined in the usual way with ABTS® after an incubation time of 30 minutes and measurement of the difference in absorbance in mA at 405 nm.

Test 2

Investigation of the binding of the antibodies to polyhaptens or fusion protein.

Microtitre plates (Nunc Co.) are incubated with 1 μg/ml polyhapten (produced according to Examples 10 and 12) or fusion protein (produced according to Example 2) in coating buffer (see Test 1). After a washing step, they are incubated with the antibody sample (mouse serum or culture supernatant). After a further washing step, the test antibody is incubated with polyclonal sheep-anti-mouse Fcγ, Fab-peroxidase conjugate, a further washing step is carried out and the peroxidase activity is determined with ABTS® analogous to Test 1. A multitude of antibodies were found which bind to the polyhapten according to Example 10 and to the fusion protein but not, however, to the polyhapten according to Example 12.

Test 3

Investigation of the binding of the antibodies to native α1-microglobulin in samples of patients' urine.

Samples of patients' urine are used whose α1-microglobulin content was measured by means of a nephelometric method or by a LC-partigen test (Behring Co.).

First the reactivity of the antibody is determined in Test 2. The specificity is examined in a competition experiment between binding of the antibody to α1-microglobulin in the patients' urine and to peptide or fusion protein bound to the wall. Antibody samples are pre-incubated with urine samples which contain increasing concentrations of α1-microglobulin or with a urine sample pool from normal donors as a negative control. Microtitre plates which are coated with 1 μg/ml polyhapten as in Test 2 are coated with the pre-incubated sample. After a washing step, the secondary antibody conjugate (sheep-anti mouse Fcγ, Fab-peroxidase conjugate, analogous to Test 1 and 2) is incubated. The quantification of the residual binding of the antibody sample to the peptide bound to the wall is measured analogous to Test 1 and 2 by determination of the peroxidase activity using ABTS®. The monoclonal antibody 6.046.75 (ECACC 90071906) according to the present invention is characterized in that it binds or recognizes the peptide according to Examples 6, 7 and 8, the fusion protein according to Example 2.1 or 2.2 and native α1-microglobulin isolated from the urine of patients. Binding to the peptide or to the fusion protein can be inhibited by pre-incubating the antibody with urine samples from patients containing α1-microglobulin. The antibody belongs to the IgGl, kappa subclass.

EXAMPLE 16

Determination of α1-microglobulin with a test strip 16.1 Construction of the test strip:

Starting Area (SA)

The starting area consists of a fleece of 100% polyester with 10% Kuralon (Binzer Co.) which has a thickness of 1.0 mm and an absorbtive capacity of 1800 ml/m$^2$.

Buffer Area (BA)

A fleece material SL 4207 KA from the Kalff Company, Euskirchen, Federal Republic of Germany, (consisting of 90% polyester, 10% staple fibre and small amounts of acrylate) which is 0.7 mm thick and has an absorptive capacity of 480 ml/m² is impregnated with the following solution and subsequently dried:

200 mmol/l sodium phosphate, pH 7.8

1% by weight bovine serum albumin

Conjugate Area (CA)

A glass fibre fleece made of 100% glass fibre strengthened with 10% Kuralon and which is 0.2 mm thick and has an absorptive capacity of 200 ml/m² is impregnated with the following solution and subsequently dried:

70 mmol/l sodium phosphate, pH 7.4

0.5% by weight bovine serum albumin 6 kU/l conjugate of β-galactosidase and analyte specific antibody (IgG)

Capture Area (CA)

A mixed fleece made of 50% polyester, 50% cotton linters and 3% Etadurin which is 0.5 mm thick and has an absorptive capacity of 450 ml/m² is impregnated with the following solution and subsequently dried:

10 mmol/l sodium phosphate, pH 7.5 thermo BSA-streptavidin (200 mg/l, produced according to EP-A 0 269 092)

The thermo BSA-streptavidin is immobilized as described in EP-A-0 374 778.

The fleece thus impregnated is subsequently impregnated again and dried with:

10 mmol/l sodium phosphate, pH 7.5 biotinylated α1M fusion protein produced according to Example 2.1 or 2.2 (1 μmol/l), biotinylation according to Example 5

Detection Area (DA)

A 0.1 mm thick polycarbonate foil is coated with a soluble film having the following composition:

4.5 g Mowiol 18/88 (Hoechst Company, Frankfurt/M. Federal Republic of Germany)

0.3 g chlorophenol-red β-D-galactoside

The areas are glued onto a carrier using a hot-setting adhesive as described in EP-A 0 374 684.

16.2 Detection of α1-Microglobulin in Aqueous Solutions Using the Described Test Strips:

Test strips made according to Example 16.1 are placed with the absorptive fleece in the sample containing α1M (e.g. urine). After 5 minutes the sample concentration is correlated with the color which appears in the detection area. Thus a yellow color is obtained with the test strips described above in solutions without analyte, an increasing red color is obtained at 5, 20, 100 mg analyte/l. In this way the analyte can be determined visually in a semiquantitative manner.

A quantitative determination is possible when the test strip is determined by remission photometry 5 minutes after application of the sample. FIG. 3 shows a calibration curve obtained by using the α1M fusion protein according to Example 2.2.

Analogous results are obtained if a biotinylated peptide (1 μmol/l) according to Example 8 is used instead of the biotinylated fusion protein.

---

We claim:

1. An isolated peptide comprising an immunogenic portion of an amino acid sequence of human $\alpha_1$ microglobulin as set forth in SEQ ID NO:11, said portion consisting of at least 6 contiguous amino acids and no more than 39 contiguous amino acids found at positions 144–183 of said $\alpha_1$ microglobulin.

2. The isolated peptide of claim 1, said portion consisting of at least 6 contiguous amino acids and no more than 25 contiguous amino acids found at positions 158–183 of said $\alpha_1$ microglobulin.

3. An isolated peptide comprising an immunogenic portion of an amino acid sequence of human $\alpha_1$ microglobulin as set forth in SEQ ID NO:12, said portion consisting of at least 6 contiguous amino acids and no more than 20 contiguous amino acids found at positions 1–20 of said human $\alpha_1$ microglobulin.

4. Isolated fusion protein comprising the peptide of claim 1 and a carrier protein moiety.

5. Isolated fusion protein comprising the peptide of claim 3 and a carrier protein moiety.

6. The isolated fusion protein of claims 4 or 5, wherein said carrier protein moiety is galactose binding protein truncated by 3 amino acids.

7. The isolated fusion protein of claims 4 or 5, coupled to a member of a specific binding pair.

8. The isolated fusion protein of claim 7, wherein said member of said specific binding pair is biotin.

9. The isolated peptide of claim 2, said portion consisting of at least 6 contiguous amino acids and no more than 22 contiguous amino acids found at positions 161–183 of said $\alpha_1$ microglobulin.

10. The isolated peptide of claim 2, said portion consisting of at least 6 contiguous amino acids and no more than 14 contiguous amino acids found at positions 169–183 of said $\alpha_1$ microglobulin.

11. The isolated peptide of claim 2, said portion consisting of at least 6 contiguous amino acids and no more than 13 contiguous amino acids found at positions 170–183 of said $\alpha_1$ microglobulin.

* * * * *

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH:      83 base pairs
      (B) TYPE:        nucleic acid
      (C) STRANDEDNESS: single
      (D) TOPOLOGY:    linear (ii) MOLECULE TYPE:
      (A) DESCRIPTION: genomic DNA (xi) SEQUENCE DESCRIPTION: SEQ ID NO: 1:

```
AATTC TTC ACC ATG GCT GAC CGT GGT GAA TGC GTC CCG GGT GAA CAG GAA      50
      Phe Thr Met Ala Asp Arg Gly Glu Cys Val Pro Gly Glu Gln Glu
       1               5                  10                  15

CCG GAA CCG ATC CTG ATC CCG CGT TAAGATCTA                              83
Pro Glu Pro Ile Leu Ile Pro Arg
                  20
```

(2) INFORMATION FOR SEQ ID NO: 2:

(i) SEQUENCE CHARACTERISTICS:
      (A) LENGTH:      1001 base pairs
      (B) TYPE:        nucleic acid
      (C) STRANDEDNESS: single
      (D) TOPOLOGY:    linear (xi) SEQUENCE DESCRIPTION: SEQ ID NO: 2:

```
GCT GAT ACT CGC ATT GGT GTA ACA ATC TAT AAG TAC GAC GAT AAC TTT        48
Ala Asp Thr Arg Ile Gly Val Thr Ile Tyr Lys Tyr Asp Asp Asn Phe
```

```
                1               5                        10                          15
     ATG TCT GTA GTG CGC AAG GCT ATT GAG CAA GAT GCG AAA GCC GCG CCA        96
     Met Ser Val Val Arg Lys Ala Ile Glu Gln Asp Ala Lys Ala Ala Pro
                      20                  25                  30

GAT GTT CAG CTG CTG ATG AAT GAT TCT CAG AAT GAC CAG TCC AAG CAG       144
     Asp Val Gln Leu Leu Met Asn Asp Ser Gln Asn Asp Gln Ser Lys Gln
                  35                  40                  45

AAC GAT CAG ATC GAC GTA TTG CTG GCC AAG GGG GTG AAG GCA CTG GCC       192
     Asn Asp Gln Ile Asp Val Leu Leu Ala Lys Gly Val Lys Ala Leu Ala
              50                  55                  60

ATC AAC CTG GTT GAC CCG GCA GCT GCG GGT ACG GTG ATT GAG AAA GCG       240
     Ile Asn Leu Val Asp Pro Ala Ala Ala Gly Thr Val Ile Glu Lys Ala
     65                  70                  75                  80

CGT GGG CAA AAC GTG CCG GTG GTT TTC TTC AAC AAA GAA CCG TCT CGT       288
     Arg Gly Gln Asn Val Pro Val Val Phe Phe Asn Lys Glu Pro Ser Arg
                          85                  90                  95

AAG GCG CTG GAT AGC TAC GAC AAA GCC TAC TAC GTT GGC ACT GAC TCC       336
     Lys Ala Leu Asp Ser Tyr Asp Lys Ala Tyr Tyr Val Gly Thr Asp Ser
                     100                 105                 110

AAA GAG TCC GGC ATT ATT CAA GGC GAT TTG ATT GCT AAA CAC TGG GCG       384
     Lys Glu Ser Gly Ile Ile Gln Gly Asp Leu Ile Ala Lys His Trp Ala
                 115                 120                 125

GCG AAT CAG GGT TGG GAT CTG AAC AAA GAC GGT CAG ATT CAG TTC GTA       432
     Ala Asn Gln Gly Trp Asp Leu Asn Lys Asp Gly Gln Ile Gln Phe Val
             130                 135                 140

CTG CTG AAA GGT GAA CCG GGC CAT CCG GAT GCA GAA GCA CGT ACC ACT       480
     Leu Leu Lys Gly Glu Pro Gly His Pro Asp Ala Glu Ala Arg Thr Thr
     145                 150                 155                 160

TAC GTG ATT AAA GAA TTG AAC GAT AAA GGC ATC AAA ACT GAA CAG TTA       528
     Tyr Val Ile Lys Glu Leu Asn Asp Lys Gly Ile Lys Thr Glu Gln Leu
                         165                 170                 175

CAG TTA GAT ACC GCA ATG TGG GAC ACC GCT CAG GCG AAA GAT AAG ATG       576
     Gln Leu Asp Thr Ala Met Trp Asp Thr Ala Gln Ala Lys Asp Lys Met
                     180                 185                 190

GAC GCC TGG CTG TCT GGC CCG AAC GCC AAC AAA ATC GAA GTG GTT ATC       624
     Asp Ala Trp Leu Ser Gly Pro Asn Ala Asn Lys Ile Glu Val Val Ile
                 195                 200                 205

GCC AAC AAC GAT GCG ATG GCA ATG GGC GCG GTT GAA GCG CTG AAA GCA       672
     Ala Asn Asn Asp Ala Met Ala Met Gly Ala Val Glu Ala Leu Lys Ala
             210                 215                 220

CAC AAC AAG TCC AGC ATT CCG GTG TTT GGC GTC GAT GCG CTG CCA GAA       720
     His Asn Lys Ser Ser Ile Pro Val Phe Gly Val Asp Ala Leu Pro Glu
     225                 230                 235                 240

GCG CTG GCG CTG GTG AAA TCC GGT GCA CTG GCG GGC ACC GTA CTG AAC       768
     Ala Leu Ala Leu Val Lys Ser Gly Ala Leu Ala Gly Thr Val Leu Asn
                         245                 250                 255

GAT GCT AAC AAC CAG GCG AAA GCG ACC TTT GAT CTG GCG AAA AAC CTG       816
     Asp Ala Asn Asn Gln Ala Lys Ala Thr Phe Asp Leu Ala Lys Asn Leu
                     260                 265                 270

GCC GAT GGT AAA GGT GCG GCT GAT GGC ACC AAC TGG AAA ATC GAC AAC       864
     Ala Asp Gly Lys Gly Ala Ala Asp Gly Thr Asn Trp Lys Ile Asp Asn
                 275                 280                 285

AAA GTG GTC CGC GTA CCT TAT GTT GGC GTA GAT AAA GAC AAC CTG GCT       912
     Lys Val Val Arg Val Pro Tyr Val Gly Val Asp Lys Asp Asn Leu Ala
             290                 295                 300

GAA TTC TTC ACC ATG GCT GAC CGT GGT GAA TGC GTC CCG GGT GAA CAG       960
     Glu Phe Phe Thr Met Ala Asp Arg Gly Glu Cys Val Pro Gly Glu Gln
     305                 310                 315                 320

GAA CCG GAA CCG ATC CTG ATC CCG CGT TAAGATCTAA GCTT                  1001
```

Glu Pro Glu Pro Ile Leu Ile Pro Arg
                325

(2) INFORMATION FOR SEQ ID NO: 3:

(i) SEQUENCE CHARACTERISTICS:
        (A) LENGTH:       80 base pairs
        (B) TYPE:         nucleic acid
        (C) STRANDEDNESS: single
        (D) TOPOLOGY:     linear (xi) SEQUENCE DESCRIPTION:   SEQ ID NO: 3:

GATCCAGGTG CTACCGAAGC TGAAATCTCC ATGACCTCCA CCCGTTGGCG TAAAGGTGTT      60

TGCGAAGAAA CCTCCGGCGC                                                 80

(2) INFORMATION FOR SEQ ID NO: 4:

(i) SEQUENCE CHARACTERISTICS:
        (A) LENGTH:       80 base pairs
        (B) TYPE:         nucleic acid
        (C) STRANDEDNESS: single
        (D) TOPOLOGY:     linear (xi) SEQUENCE DESCRIPTION:   SEQ ID NO: 4:

CTACGAAAAA ACCGACACCG ACGGTAAATT CACCATGGCT GACCGTGGTG AATGCGTCCC      60

GGGTGAACAG GAACCGGAAC                                                 80

(2) INFORMATION FOR SEQ ID NO: 5:

(i) SEQUENCE CHARACTERISTICS:
        (A) LENGTH:       30 base pairs
        (B) TYPE:         nucleic acid
        (C) STRANDEDNESS: single
        (D) TOPOLOGY:     linear (xi) SEQUENCE DESCRIPTION:   SEQ ID NO: 5:

CGATCCTGAT CCCGCGTTAA GATCTAGATA                                      30

(2) INFORMATION FOR SEQ ID NO: 6:

(i) SEQUENCE CHARACTERISTICS:
        (A) LENGTH:       77 base pairs
        (B) TYPE:         nucleic acid
        (C) STRANDEDNESS: single
        (D) TOPOLOGY:     linear (xi) SEQUENCE DESCRIPTION:   SEQ ID NO: 6:

AGCTTATCTA GATCTTAACG CGGGATCAGG ATCGGTTCCG GTTCCTGTTC ACCCGGGACG      60

CATTCACCAC GGTCAGC                                                    77

(2) INFORMATION FOR SEQ ID NO: 7:

(i) SEQUENCE CHARACTERISTICS:
        (A) LENGTH:       80 base pairs
        (B) TYPE:         nucleic acid
        (C) STRANDEDNESS: single
        (D) TOPOLOGY:     linear (xi) SEQUENCE DESCRIPTION:   SEQ ID NO: 7:

CATGGTGAAT TTACCGTCGG TGTCGGTTTT TTCGTAGGCG CCGCAGGTTT CTTCGCAAAC      60

ACCTTTACGC CAACGGGTGG                                                 80

(2) INFORMATION FOR SEQ ID NO: 8:

```
        (i) SEQUENCE CHARACTERISTICS:
            (A) LENGTH:      33 base pairs
            (B) TYPE:        nucleic acid
            (C) STRANDEDNESS: single
            (D) TOPOLOGY:    linear (xi) SEQUENCE DESCRIPTION: SEQ ID NO: 8:

AGGTCATGGA GATTTCAGCT TCGGTAGCAC CTG                                       33

(2) INFORMATION FOR SEQ ID NO: 9:

(i) SEQUENCE CHARACTERISTICS:
            (A) LENGTH:      1112 base pairs
            (B) TYPE:        nucleic acid
            (C) STRANDEDNESS: single
            (D) TOPOLOGY:    linear (xi) SEQUENCE DESCRIPTION: SEQ ID NO: 9:

GCT GAT ACT CGC ATT GGT GTA ACA ATC TAT AAG TAC GAC GAT AAC TTT             48
Ala Asp Thr Arg Ile Gly Val Thr Ile Tyr Lys Tyr Asp Asp Asn Phe
  1               5                  10                  15

ATG TCT GTA GTG CGC AAG GCT ATT GAG CAA GAT GCG AAA GCC GCG CCA             96
Met Ser Val Val Arg Lys Ala Ile Glu Gln Asp Ala Lys Ala Ala Pro
                 20                  25                  30

GAT GTT CAG CTG CTG ATG AAT GAT TCT CAG AAT GAC CAG TCC AAG CAG            144
Asp Val Gln Leu Leu Met Asn Asp Ser Gln Asn Asp Gln Ser Lys Gln
             35                  40                  45

AAC GAT CAG ATC GAC GTA TTG CTG GCC AAG GGG GTG AAG GCA CTG GCC            192
Asn Asp Gln Ile Asp Val Leu Leu Ala Lys Gly Val Lys Ala Leu Ala
         50                  55                  60

ATC AAC CTG GTT GAC CCG GCA GCT GCG GGT ACG GTG ATT GAG AAA GCG            240
Ile Asn Leu Val Asp Pro Ala Ala Ala Gly Thr Val Ile Glu Lys Ala
 65                  70                  75                  80

CGT GGG CAA AAC GTG CCG GTG GTT TTC TTC AAC AAA GAA CCG TCT CGT            288
Arg Gly Gln Asn Val Pro Val Val Phe Phe Asn Lys Glu Pro Ser Arg
                 85                  90                  95

AAG GCG CTG GAT AGC TAC GAC AAA GCC TAC TAC GTT GGC ACT GAC TCC            336
Lys Ala Leu Asp Ser Tyr Asp Lys Ala Tyr Tyr Val Gly Thr Asp Ser
            100                 105                 110

AAA GAG TCC GGC ATT ATT CAA GGC GAT TTG ATT GCT AAA CAC TGG GCG            384
Lys Glu Ser Gly Ile Ile Gln Gly Asp Leu Ile Ala Lys His Trp Ala
        115                 120                 125

GCG AAT CAG GGT TGG GAT CTG AAC AAA GAC GGT CAG ATT CAG TTC GTA            432
Ala Asn Gln Gly Trp Asp Leu Asn Lys Asp Gly Gln Ile Gln Phe Val
    130                 135                 140

CTG CTG AAA GGT GAA CCG GGC CAT CCG GAT GCA GAA GCA CGT ACC ACT            480
Leu Leu Lys Gly Glu Pro Gly His Pro Asp Ala Glu Ala Arg Thr Thr
145                 150                 155                 160

TAC GTG ATT AAA GAA TTG AAC GAT AAA GGC ATC AAA ACT GAA CAG TTA            528
Tyr Val Ile Lys Glu Leu Asn Asp Lys Gly Ile Lys Thr Glu Gln Leu
                165                 170                 175

CAG TTA GAT ACC GCA ATG TGG GAC ACC GCT CAG GCG AAA GAT AAG ATG            576
Gln Leu Asp Thr Ala Met Trp Asp Thr Ala Gln Ala Lys Asp Lys Met
            180                 185                 190

GAC GCC TGG CTG TCT GGC CCG AAC GCC AAC AAA ATC GAA GTG GTT ATC            624
Asp Ala Trp Leu Ser Gly Pro Asn Ala Asn Lys Ile Glu Val Val Ile
        195                 200                 205

GCC AAC AAC GAT GCG ATG GCA ATG GGC GCG GTT GAA GCG CTG AAA GCA            672
Ala Asn Asn Asp Ala Met Ala Met Gly Ala Val Glu Ala Leu Lys Ala
    210                 215                 220

CAC AAC AAG TCC AGC ATT CCG GTG TTT GGC GTC GAT GCG CTG CCA GAA            720
His Asn Lys Ser Ser Ile Pro Val Phe Gly Val Asp Ala Leu Pro Glu
```

```
                225                 230                 235                 240
GCG CTG GCG CTG GTG AAA TCC GGT GCA CTG GCG GGC ACC GTA CTG AAC        768
Ala Leu Ala Leu Val Lys Ser Gly Ala Leu Ala Gly Thr Val Leu Asn
                    245                 250                 255

GAT GCT AAC AAC CAG GCG AAA GCG ACC TTT GAT CTG GCG AAA AAC CTG        816
Asp Ala Asn Asn Gln Ala Lys Ala Thr Phe Asp Leu Ala Lys Asn Leu
                260                 265                 270

GCC GAT GGT AAA GGT GCG GCT GAT GGC ACC AAC TGG AAA ATC GAC AAC        864
Ala Asp Gly Lys Gly Ala Ala Asp Gly Thr Asn Trp Lys Ile Asp Asn
                275                 280                 285

AAA GTG GTC CGC GTA CCT TAT GTT GGC GTA GAT AAA GAC AAC CTG GCT        912
Lys Val Val Arg Val Pro Tyr Val Gly Val Asp Lys Asp Asn Leu Ala
                290                 295                 300

GAA TTC CGG GAT CCA GGT GCT ACC GAA GCT GAA ATC TCC ATG ACC TCC        960
Glu Phe Arg Asp Pro Gly Ala Thr Glu Ala Glu Ile Ser Met Thr Ser
305                 310                 315                 320

ACC CGT TGG CGT AAA GGT GTT TGC GAA GAA ACC TCC GGC GCC TAC GAA       1008
Thr Arg Trp Arg Lys Gly Val Cys Glu Glu Thr Ser Gly Ala Tyr Glu
                325                 330                 335

AAA ACC GAC ACC GAC GGT AAA TTC ACC ATG GCT GAC CGT GGT GAA TGC       1056
Lys Thr Asp Thr Asp Gly Lys Phe Thr Met Ala Asp Arg Gly Glu Cys
                340                 345                 350

GTC CCG GGT GAA CAG GAA CCG GAA CCG ATC CTG ATC CCG CGT TAA GAT       1104
Val Pro Gly Glu Gln Glu Pro Glu Pro Ile Leu Ile Pro Arg
                355                 360                 365

CTA AGC TT                                                             1112

(2) INFORMATION FOR SEQ ID NO: 10:

(i) SEQUENCE CHARACTERISTICS:
         (A) LENGTH:      83 base pairs
         (B) TYPE:        nucleic acid
         (C) STRANDEDNESS: single
         (D) TOPOLOGY:    linear (ii) MOLECULE TYPE:
         (A) DESCRIPTION: genomic DNA (xi) SEQUENCE DESCRIPTION:   SEQ ID NO: 10:

AGCTTAGATC  TTAACGCGGG  ATCAGGATCG  GTTCCGGTTC  CTGTTCACCC  GGGACGCATT  60

CACCACGGTC  AGCCATGGTG  AAG                                             83

(2) INFORMATION FOR SEQ ID NO: 11:

(i) SEQUENCE CHARACTERISTICS:
         (A) LENGTH:      40 amino and residues
         (B) TYPE:        amino acid
         (C) TOPOLOGY:    linear (ii) MOLECULE TYPE:
         (A) DESCRIPTION: protein (xi) SEQUENCE DESCRIPTION:   SEQ ID NO: 11:

Gln Asp Phe Arg Val Val Ala Gln Gly Val Gly Ile Pro Glu Asp Ser
144                 150                 155

Ile Phe Thr Met Ala Asp Arg Gly Glu Cys Val Pro Gly Glu Gln Glu
160                 165                 170                 175

Pro Glu Pro Ile Leu Ile Pro Arg
                180

(2) INFORMATION FOR SEQ ID NO: 12:
```

```
    (i) SEQUENCE CHARACTERISTICS:
        (A) LENGTH:      20 amino acid residues
        (B) TYPE:        amino acid
        (C) TOPOLOGY:    linear (ii) MOLECULE TYPE:;
        (A) DESCRIPTION: protein (xi) SEQUENCE DESCRIPTION:   SEQ ID NO: 12:

Gly Pro Val Pro Thr Pro Pro Asp Asn Ile Gln Val Gln Glu Asn Phe
                 5                  10                  15

Asn Ile Ser Arg
         20

(2) INFORMATION FOR SEQ ID NO: 13:

(i) SEQUENCE CHARACTERISTICS:
        (A) LENGTH:      16
        (B) TYPE:        amino acid
        (C) STRANDEDNESS: single
        (D) TOPOLOGY:    linear (xi) SEQUENCE DESCRIPTION:   SEQ ID NO: 13:

Cys Xaa Val Pro Gly Glu Gln Glu Pro Glu Pro Ile Leu Ile Pro Arg
                 5                  10                  15

(2) INFORMATION FOR SEQ ID NO: 14:

(i) SEQUENCE CHARACTERISTICS:
        (A) LENGTH:      15
        (B) TYPE:        amino acid
        (C) STRANDEDNESS: single
        (D) TOPOLOGY:    linear (xi) SEQUENCE DESCRIPTION:   SEQ ID NO: 14:

Cys Val Pro Gly Glu Gln Glu Pro Glu Pro Ile Leu Ile Pro Arg
                 5                  10                  15

(2) INFORMATION FOR SEQ ID NO: 15:

(i) SEQUENCE CHARACTERISTICS:
        (A) LENGTH:      16
        (B) TYPE:        amino acid
        (C) STRANDEDNESS: single
        (D) TOPOLOGY:    linear (xi) SEQUENCE DESCRIPTION:   SEQ ID NO: 15:

Cys Xaa Val Pro Gly Glu Gln Glu Pro Glu Pro Ile Leu Ile Pro Arg
                 5                  10                  15

(2) INFORMATION FOR SEQ ID NO: 16:

(i) SEQUENCE CHARACTERISTICS:
        (A) LENGTH:      19
        (B) TYPE:        amino acid
        (C) STRANDEDNESS: single
        (D) TOPOLOGY:    linear (xi) SEQUENCE DESCRIPTION:   SEQ ID NO: 16:

Cys Gly Ala Tyr Glu Lys Thr Asp Thr Asp Gly Lys Phe Leu Tyr His
                 5                  10                  15

Lys Ser Lys (2) INFORMATION FOR SEQ ID NO: 17:

(i) SEQUENCE CHARACTERISTICS:
        (A) LENGTH:      20
```

```
            (B) TYPE:          amino acid
            (C) STRANDEDNESS: single
            (D) TOPOLOGY:      linear (xi) SEQUENCE DESCRIPTION:    SEQ ID NO: 17:

Cys Xaa Gly Ala Tyr Glu Lys Thr Asp Thr Asp Gly Lys Phe Leu Tyr
                 5                  10                  15

His Lys Ser Lys
            20

(2) INFORMATION FOR SEQ ID NO: 18:

(i) SEQUENCE CHARACTERISTICS:
            (A) LENGTH:        17
            (B) TYPE:          amino acid
            (C) STRANDEDNESS: single
            (D) TOPOLOGY:      linear (xi) SEQUENCE DESCRIPTION:    SEQ ID NO: 18:

Gly Pro Val Pro Thr Pro Pro Asp Asn Ile Gln Val Gln Glu Asn Phe
                 5                  10                  15

Cys
```